United States Patent [19]

Narayanan et al.

[11] Patent Number: 5,132,108
[45] Date of Patent: Jul. 21, 1992

[54] RADIOFREQUENCY PLASMA TREATED POLYMERIC SURFACES HAVING IMMOBILIZED ANTI-THROMBOGENIC AGENTS

[75] Inventors: Pallassana V. Narayanan, Davie; Kimberly D. Stanley, Florida City, both of Fla.

[73] Assignee: Cordis Corporation, Miami Lakes, Fla.

[21] Appl. No.: 610,548

[22] Filed: Nov. 8, 1990

[51] Int. Cl.⁵ .................... A61L 33/00; A61K 35/62; A61K 31/725; B05D 3/06
[52] U.S. Cl. .................... 424/78.17; 424/422; 424/423; 427/40; 427/41; 525/54.1; 525/54.2; 525/406; 525/423; 525/424; 525/430; 525/449; 525/453; 525/454; 525/474; 525/937; 604/96; 604/239
[58] Field of Search .................... 424/28, 79, 422, 423; 427/39-41

[56] References Cited

U.S. PATENT DOCUMENTS

| | | | |
|---|---|---|---|
| 4,116,898 | 9/1978 | Dudley et al. | 424/83 |
| 4,131,691 | 12/1978 | Morley et al. | 427/41 |
| 4,261,806 | 4/1981 | Asai et al. | 204/165 |
| 4,265,927 | 5/1981 | Ericksson et al. | 514/56 |
| 4,266,999 | 5/1981 | Baier | 156/227 |
| 4,326,532 | 4/1982 | Hammar | 128/349 R |
| 4,613,517 | 9/1986 | Williams et al. | 427/2 |
| 4,632,842 | 12/1986 | Karwoski et al. | 427/2 |
| 4,656,083 | 4/1987 | Hoffman et al. | 428/265 |
| 4,692,347 | 9/1987 | Yasuda | 427/40 |
| 4,846,101 | 7/1989 | Montgomery et al. | 118/723 |
| 4,919,659 | 4/1990 | Horbett et al. | 435/240.243 |
| 4,948,628 | 8/1990 | Montgomery et al. | 427/39 |

*Primary Examiner*—Thurman K. Page
*Assistant Examiner*—E. J. Webman
*Attorney, Agent, or Firm*—Lockwood, Alex, Fitzgibbon & Cummings

[57] ABSTRACT

Polymeric surfaces of medical devices or components of medical devices are provided that have enhanced biocompatibility properties. The polymeric surface presents an anti-thrombogenic, fibrinolytic or thrombolytic interface with body fluids such as blood during implantation or medical procedures. The biocompatibility enhancing agent is secured to the polymeric substrate by a spacer molecule which is covalently bound to the polymeric substrate which had been subjected to radiofrequency plasma treatment with a water vapor medium.

14 Claims, No Drawings

RADIOFREQUENCY PLASMA TREATED POLYMERIC SURFACES HAVING IMMOBILIZED ANTI-THROMBOGENIC AGENTS

BACKGROUND AND DESCRIPTION OF THE INVENTION

The present invention generally relates to enhancing the biocompatibility of polymeric surfaces as well as to medical devices or the like which include such biocompatibility-enhanced surfaces. More particularly, the invention relates to surface activation of polymeric surfaces by radiofrequency plasma treatment for the immobilization of anti-thrombogenic agents or the like on the polymeric surfaces. The radiofrequency plasma medium is one including water vapor in substantial concentrations, which medium when subjected to radiofrequency plasma discharge conditions activates the polymeric surface for attachment thereto of anti-thrombogenic agents such as heparinous materials and the like.

It is of course well known that it is important for many medical devices to have surfaces which are of enhanced biocompatibility. It is also well known that, generally speaking, biocompatibility properties are enhanced by attempting to secure anti-thrombogenic agents to polymeric surfaces of medical devices, particularly those which are blood contacting surfaces to be implanted or otherwise used during medical procedures and the like. In many instances, it is particularly undesirable to have the anti-thrombogenic agent leach away in wet environments such as are encountered by medical devices that engage blood or other body fluids.

Certain attempts have been made and approaches have been suggested whereby a polymeric surface is activated by treatment with a plasma which in turn reacts with heparin or the like to provide a polymeric surface having anti-thrombogenic properties. Included are patents incorporating plasma discharge treatment with a gaseous environment including a variety of gases, including inert gases and organic gases. Patents in this regard include U.S. Pat. Nos. 4,613,517, 4,656,083 and 4,948,628, which mention a variety of plasma media including those generated from hydrogen, helium, ammonia, nitrogen, oxygen, neon, argon, krypton, zenon, ethylenic monomers and other hydrocarbons, halohydrocarbons, halocarbons and silanes. It will be appreciated that various ones of these plasma media are relatively expensive and can be hazardous to use within a manufacturing environment and/or to dispose of as waste. Also, certain plasma media are more suitable for treatment of specific substrates.

Other surface treatments have been proposed that are said to activate polymeric surfaces for immobilization of anti-thrombogenic agents. Included are procedures which incorporate chromic acid treatments or flame oxidation procedures. Approaches of this type tend to be especially suitable for particular polymeric surfaces but not for others, and they can adversely affect the bulk properties of the polymeric material thus treated. Procedures of this general type have further disadvantages in that the particular geometry of the medical device or the like being treated must be taken into consideration in order to reach the surfaces requiring treatment.

It is desirable to provide a surface treatment procedure which is available for use in connection with rendering anti-thrombogenic any of a number of surfaces of medical devices or the like. It is further desirable that any plasma deposition procedure included in this regard avoid the need to use plasma media that are expensive, potentially hazardous or otherwise difficult to handle. At the same time, any plasma media should strongly bind the anti-thrombogenic agent to the surface being treated, preferably while also accomplishing this in an especially efficient manner that is readily susceptible to use on a large scale.

It has been discovered that plasma media which include a substantial concentration of water vapor, either alone or in combination with oxygen gas, provide an especially advantageous activation of numerous polymeric surfaces that are subjected to radiofrequency plasma treatment conditions in the environment of these media. A particularly simplified and efficient surface activation is achieved when the thus activated surface is treated with a spacer component having amine moieties, particularly spacer components which have primary or secondary amine groups. An anti-thrombogenic agent or the like, typically with the assistance of a coupling agent, is covalently bound to the spacer component. The result is an evenly covered biocompatible surface that significantly avoids leaching of the anti-thrombogenic agent or the like away from the medical device or the like.

It is accordingly a general object of the present invention to provide an improved method for treating polymeric surfaces and medical articles or the like having such surfaces.

Another object of the present invention is to provide improved medical device components having polymeric surfaces with anti-thrombogenic agents or the like immobilized thereon.

Another object of this invention is to provide an improved anti-thrombogenic polymeric surface and method of making same which utilizes radiofrequency plasma discharge techniques that avoid the use of expensive or hazardous plasma media.

Another object of the present invention is to provide an improved method for covalently binding anti-thrombogenic agents or the like to polymeric surfaces, which agents do not leach away in wet environments, as well as to the improved polymeric surfaces thus produced.

Another object of this invention is to provide an improved process for rendering medical device polymeric surfaces anti-thrombogenic through a process that is relatively independent of the particular polymeric surface and of the shape or geometry thereof.

These and other objects, features and advantages of this invention will be clearly understood through a consideration of the following detailed description.

DESCRIPTION OF THE PARTICULAR EMBODIMENTS

The present invention is particularly suitable in connection with medical device articles including catheters, cannulas, balloons for use on catheters or the like, guidewires and any other device having operational requirements and properties that can be improved by attaching an anti-thrombogenic, fibrinolytic or thrombolytic agent to one or more surfaces of the device. Typically these types of devices or at least surfaces thereof are made of polymeric materials. In the event that the surface to be treated in accordance with this invention is made of some other material, a thin layer of a suitable polymeric material first can be applied to the surface to be treated.

Polymers which are suitable for use as the surface to be modified with an anti-thrombogenic agent or the like in accordance with the present invention include various polyurethane components including polyurethanes and polyurethane copolymers. Included are polyurethane-polyester copolymers, polyurethane-polyether copolymers and nylon-polyether copolymers. Other polymers which can be treated according to the invention include silastic silicone rubber and the like. The selected polymer must have overall properties which, except for thrombus concerns, render the polymers suitable for the surface of a medical device made in accordance with the present invention.

In accordance with the invention, these types of polymeric surfaces are made more suitable for long-term or short-term contact with flowing blood or other body fluids. This is accomplished by attaching an anti-thrombogenic agent, fibrinolytic agent or thrombolytic agent to the surface or device. These agents are used in relatively small amounts, and they are attached in such a manner that they remain biologically active, while at the same time being affixed to the polymeric surface in so secure a manner that the agents will not leach away in wet in vitro or in vivo environments.

Securement of the anti-thrombogenic agent or the like onto the polymeric surface includes positioning the polymeric surface within a radiofrequency plasma discharge environment. Devices for providing such an environment are generally known in the art. Typical devices in this regard are shown, for example, in U.S. Pat. Nos. 4,632,842 and 4,656,083, the subject matter thereof being incorporated by reference hereinto. In such devices, a reactor chamber is provided, and the substrate surface to be treated is inserted into the chamber. A source of fluid which provides the plasma environment is fed into the chamber, typically after the chamber is evacuated by a suitable vacuum pump or the like. Glow discharge is induced within the reactor chamber by an electrode assembly disposed about the chamber. For example, when the chamber is generally cylindrically shaped, the electrode assembly can include a pair of band electrodes that are mounted on a travelling block which moves along a designated length of the reactor chamber. The electrode assembly can include instead a radiofrequency coil or the like. After the flow of treating medium or fluid has been established, glow discharge is initiated by generating a radiofrequency electric field within the reactor chamber, thereby inducing treatment of the polymeric surface. The radiofrequency electric field can be applied to the chamber either capacitively or inductively.

In accordance with the present invention, the treating fluid or plasma medium is a water vapor medium which is provided within the chamber. When the radiofrequency electric field is applied to this water vapor medium, reactive species are created. The reactive species, when they encounter the polymeric surface, react with atoms and/or molecules of the polymeric material, thereby modifying the chemical nature of the surface. It is believed that the polymeric surface is modified by causing the formation of carboxyl groups and/or hydroxyl groups on the surface of the polymeric material.

With more particular reference to the treating fluid or plasma medium, air or other gas is first evacuated from the radiofrequency treatment chamber until virtually no air or other gas remains therewithin. Then the water vapor is pumped or otherwise injected into the chamber. It is also possible to mix oxygen with the water and/or water vapor which is believed to further enhance the efficiency of the surface modification carried out in accordance with this aspect of the invention. The atmosphere within the chamber can be 100 percent water vapor, based upon the total volume of the fluid within the chamber, and as low as about 40 percent by volume of water vapor when oxygen is mixed therewith. When oxygen is included in the plasma gas within the chamber, the preferred volume of water vapor is between about 40 and about 90 volume percent, with the balance being oxygen. It will be appreciated by those familiar with plasma discharge techniques that these volume percents are as present within the chamber at an instant in time because these are flowing fluids.

When a polymeric surface such as silastic (silicone rubber) is to be treated with this water vapor or water vapor/oxygen plasma, it is preferred to pretreat the silicone rubber surface. A suitable pretreatment is within an inert gas plasma such as argon and the like. Suitable reactive species are formed thereafter with the water vapor or water vapor and oxygen plasma as discussed herein.

The resulting reactive species-modified polymeric surface is then treated with a spacer molecule which provides reactive sites for attachment of the anti-thrombogenic agent or the like thereto and thus to polymeric surface. Preferred spacer molecules are those which contain primary or secondary amine groups. Exemplary molecules having suitable spacer groups include albumin, streptokinase, urokinase, polyethyleneimine (PEI) and the like, and combinations thereof.

Covalent linkages between the reactive sites (typically carboxyl groups) on the polymeric surface and the amine groups of the spacer molecule are formed. Generally speaking, the covalent linkages are accomplished by a condensation or trans-esterification reaction therebetween, often while using a suitable coupling agent. Typical coupling agents in this regard include 1-ethyl-3-(3-dimethylaminopropyl)-carbodiimide hydrochloride (EDC), dicyclohexyl carbodiimide (DCC) or other known coupling agents and the like.

The spacer components are typically applied in solution form. For example, a spacer component such as polyethyleneimine can be utilized within a water solution containing approximately one percent by weight of PEI. Typically, the spacer component will be present at a concentration between about 1.0 and about 5.0 weight percent, based upon the weight of spacer solution.

A suitable anti-thrombogenic, fibrinolytic or thrombolytic agent is then covalently bound to the spacer group, also by means of condensation or transesterification chemistry. It is preferred that the agent exhibit acid functionality, whereby the carboxyl groups form a covalent linkage with amine groups of the spacer component. The resultant device has an evenly covered anti-thrombogenic surface from which the anti-thrombogenic agent does not readily leach.

Exemplary anti-thrombogenic agents include heparinous components such as heparin, hirudin, heparin-albumin conjugates, hyaluronic acid, and the like. Illustrative fibrinolytic or thrombolytic agents include streptokinase, urokinase and the like. Combinations of a spacer component and of an anti-thrombogenic agent or the anti-thrombogenic agent by itself can be used in the anti-thrombogenic agent composition which is attached to the modified polymeric surface having reactive sites.

The anti-thrombogenic agent or the like is applied in the form of a solution having between about 10 and about 20 weight percent of the anti-thrombogenic, fibrinolytic or thrombolytic agent, based upon the total weight of the composition.

The following examples illustrate the process and product, as well as performance results.

EXAMPLE 1

A polyurethane-polyester copolymer surface was subjected to radiofrequency plasma treatment by subjecting same to a radiofrequency electric field in the presence of a water vapor plasma medium. An aqueous solution containing 1% polyethyleneimine and 3 milligrams of PEI per milliliter of ethyldimethylaminopropyl carbodiimide coupling agent was applied to the radiofrequency plasma discharge modified polyurethane surface, and the reaction time for this step was five minutes. The surface was thereafter well rinsed with deionized water and allowed to air dry.

An aqueous solution of heparin and ethyldimethylaminopropyl carbodiimide containing 5 milligrams of heparin per milliliter of solution and 7.5 milligrams of EDC per milliliter of solution at a pH of 3 was then applied to the PEI-treated surface. Treatment proceeded for one hour, the reaction being at room temperature, after which the samples were well rinsed and allowed to dry in order to provide a polymeric surface having an anti-thrombogenic agent secured to its surface.

EXAMPLE 2

Samples (in triplicate) of polyurethane devices treated in accordance with Example 1 were subjected to in vitro testing. Each sample (and a corresponding control) was immersed in five milliliters of phosphate buffered saline solution (PBS) at a pH of 7.4. Each extraction was run for one of the following extraction times: fifteen minutes, thirty minutes, forty-five minutes, one hour, three hours, twenty-four hours, forty-eight hours and seventy-two hours. Each sample and control was contacted with toluidine blue to determine the presence of heparin. Each of the samples stained purple, which indicates the presence of heparin on the surface of each of them. The intensity of the staining did not vary from the initial samples to those extracted for seventy-two hours. The controls, which were heparinized and extracted in PBS, exhibited no signs of color change upon staining.

EXAMPLE 3

Samples of substrates treated in accordance with Example 1 were subjected to in vitro extraction conditions in 4M guanidine hydrochloride for one hour at room temperature. Other virtually identical samples were not subjected to extraction conditions. The extract was then assayed using a dimethylmethylene blue colorimetric assay which measures the purple shift in the presence of heparin. The extracted samples were also stained with toluidine blue to detect any heparin that might have been present. No heparin concentration was evident in the guanidine extract, which indicates that no heparin was removed by the guanidine. All of the extracted samples stained purple in toluidine blue with no variation in intensity from the non-extracted samples.

EXAMPLE 4

Samples were made substantially in accordance with Example 1, except radiolabeled heparin was used. The heparin was labeled using $^{99m}Tc$. The samples were counted using a gamma counter, and calculations were performed to determine the actual amount of heparin on the surface of the polymer. The counter detected an initial concentration of heparin of from 8 to 10 micrograms per square centimeter. After extraction with human blood plasma at 37° C. for three hours, the heparin concentration was detected at from 5 to 8 micrograms per square centimeter.

EXAMPLE 5

Samples made in accordance with Example 1 were subjected to enzyme-linked immunosorbent assay testing for AT-III binding. This testing procedure, identified as ELISA was as follows. Heparin coated samples were incubated in human blood plasma with AT-III. The AT-III binds to the active site of the heparin. Another solution which contained anti-AT-III conjugated with peroxidase was then allowed to incubate. When the excess was rinsed away, the enzyme substrate and chromogen were added which forms an intense color in the presence of the anti-AT-III conjugate. The color change is directly proportional to the active heparin on the surface. By this testing procedure, the biological activity of the covalently bound heparin was evaluated. This testing confirmed that the heparin on the samples was able to bind AT-III, indicating that the immobilized heparin retains its biological activity with an absorbance value well above the background value for this test.

EXAMPLE 6

Samples made in accordance with Example 1 were subjected to in vivo testing using a known method (J. D. Martinson and R. N. Schaap, *Transactions American Society for Artificial Internal Organs*, Vol. XXVI, 1980, page 284). In this test, the samples, which were catheters coated in accordance with Example 1, were exposed to blood for thirty minutes. The resultant thrombus was quantified gravimetrically, and the results were reported as a function of the exposed surface area. The results indicated that the catheters heparinized in accordance with the present invention were 5.5 times less thrombogenic than the uncoated polyurethane catheters.

EXAMPLE 7

Several samples of a polyurethane-polyester copolymer in the form of a catheter were loaded into an RF plasma reactor. The reactor was pumped down to below 1 mtorr, water vapor and oxygen were brought into the reactor until the pressure rose to the 200–400 mtorr range, and an RF power of 20 watts was applied to create a plasma. A number of runs were made, with the plasmas varying from 80% water vapor and 20% oxygen to 50% water vapor and 50% oxygen, as measured by a gas analyzer. The samples were treated for about 20 seconds and heparinized as in Example 1 and stained with toluidine blue.

A second type of sample was treated in the same way as the first ones, except that there was no oxygen brought into the reactor. This sample was heparinized and stained with toluidine blue. A third type of sample was treated with only oxygen plasma, and this sample was heparinized and stained with toluidine blue.

It was found that the sample which was oxygen plasma treated and subsequently heparinized gave a non-uniform staining compared to the water plasma-or water/oxygen plasma-treated samples. Each of the water plasma-and water/oxygen-plasma treated samples showed uniform staining, but the water/oxygen plasma-treated and subsequently heparinized sample showed a more intense staining than the sample treated in water plasma only and heparinized subsequently.

EXAMPLE 8

A polyurethane-polyether copolymer (Pellethane) substrate was treated with a water/oxygen plasma a 4:1 ratio following the procedure described in Example 7 and subsequently heparinized as in Example 1. The he sample was tested for covalent binding of heparin with positive results.

EXAMPLE 9

A nylon-polyether copolymer (Vestamid from Huls) was treated with a water/oxygen plasma as described in Example 7 and heparinized as in Example 1, except that the PEI in Example 1 was replaced with albumin as the spacer. The plasma blend was varied on a number of samples from 5% water vapor and 25% oxygen to 50% water vapor and 50% oxygen and blends therebetween. The heparinized sample was tested for covalent binding with positive results.

EXAMPLE 10

A silastic silicone rubber tubing was treated in an argon plasma and subsequently treated in a 75% water/25% oxygen plasma. Another sample was treated with a 75% water/25% oxygen plasma without an argon plasma pretreatment. Both samples were heparinized as in Example 1 three weeks after the plasma treatment. The sample which was pretreated in argon plasma before water/oxygen plasma showed a uniform intense staining when tested for the presence of heparin using toluidine blue, while the sample which was not given an argon plasma pretreatment showed a uniform staining, but not as intense as that subjected to the pretreatment. Another silastic tubing which was treated in an oxygen-only plasma did not show any presence of heparin, even when heparinization was attempted within a few hours of this plasma treatment.

EXAMPLE 11

A nylon-polyether copolymer substrate was treated in a water/oxygen plasma. The treated surface was coated with a film of PEI as in Example 1. This surface was coated with a film of hyaluronic acid, which is an anti-thrombogenic agent. The coated surface was tested for covalent binding of hyaluronic acid with positive results.

It will be understood that the embodiments of the present invention which have been described are illustrative of some of the applications of the principles of the present invention. Numerous modifications may be made by those skilled in the art without departing from the true spirit and scope of the invention.

We claim:

1. A method for enhancing the biocompatibility of medical device polymeric surfaces, comprising the steps of:

positioning a polymeric surface within a radiofrequency plasma discharge environment;

inserting fluid into said radiofrequency plasma discharge environment to provide plasma medium having between about 40 and about 90 volume percent water vapor, the balance of said fluid, between about 10 and about 60 volume percent being oxygen, based on the total volume of the plasma medium;

subjecting said plasma medium within the environment to radiofrequency electric field in order to form reactive species from said fluid within the environment and to have the reactive species react with the polymeric surface to form a modified polymeric surface having reactive sites;

treating said modified polymeric surface with a spacer component having amine groups, said treating step being in the presence of a coupling agent, whereby covalent linkages are formed between the spacer component amine groups and the reactive sites of the modified polymeric surface; and contacting an anti-thrombogenic, fibrinolytic or thrombolytic agent having acid functionality and biologically active properties with said spacer component-treated modified polymeric surface, whereby said medical device polymeric surface exhibits biocompatibility improvements over said polymeric surface which is not treated according to the method, and whereby said biocompatible medical device polymeric surface anti-thrombogenic, fibrinolytic or thrombolytic agent is resistant to extraction under in vivo conditions while retaining its biologically active properties.

2. The method in accordance with claim 1, wherein said treating step utilizes a spacer component which is an amine selected rom the group consisting of primary amines, secondary amines, and combinations thereof.

3. The method in accordance with claim 1, wherein said reactive sites formed by said subjecting step include carboxyl groups, hydroxyl groups or combinations thereof.

4. The method in accordance with claim 1, wherein said reactive sites formed by said subjecting step include carboxyl groups thereof.

5. The method in accordance with claim 1, wherein said contacting step contacts said spacer component-treated modified polymeric surface with a heparinous component.

6. The method in accordance with claim 1, wherein said plasma discharge environment is evacuated prior to said water vapor inserting step.

7. A method for enhancing the biocompatibility of medical device polymeric surfaces, comprising the steps of:

positioning a polymeric surface within a radiofrequency plasma discharge environment;

inserting fluid into said radiofrequency plasma discharge environment to provide a plasma medium having between about 40 and about 100 volume percent water vapor and between about 0 and about 60 volume percent oxygen, based on the total volume of the plasma medium;

subjecting said plasma medium within the environment to a radiofrequency electric field in order to form reactive species from said fluid within the environment and to have the reactive species react with the polymeric surface to form a modified polymeric surface having reactive sites;

treating said modified polymeric surface with a spacer component having amine groups, said treating step being in the presence of a coupling agent, whereby covalent linkages are formed between the spacer component amine groups and the reactive sites of the modified polymeric surface;

contacting an anti-thrombogenic, fibrinolytic or thrombolytic agent having acid funtionality and biologically active properties with said spacer component-treated modified polymeric surface, whereby said medical device polymeric surface exhibits biocompatibility improvement over said polymeric surface which is not treated according to the method, and whereby said biocompatible medical device polymeric surface anti-thrombogenic, fibrinolytic or thrombolytic agent is resistant to extraction under in vivo conditions while retaining its biologically active properties; and said positioning step is preceded by pretreating a silicone rubber polymeric surface with an inert gas plasma procedure.

8. A medical device having a biocompatible polymeric surface, wherein said biocompatible polymeric surface comprises a surface which has been modified by subjecting the polymeric surface to radiofrequency discharge treatment within a plasma medium having between about 40 and about 90 volume percent water vapor, the balance of said plasma medium being between about 10 and about 60 volume percent oxygen based upon the total volume of plasma medium, followed by treatment with a coupling agent and a spacer component having amine groups forming covalent linkages with the polymeric surfaces which had been subjected to radiofrequency discharge treatment with said plasma medium, and then by treatment with an anti-thrombogenic, fibrinolytic or thrombolytic agent having acid functionality contacting and covalently bonding with the spacer component-treated polymeric surface to provide the biocompatible polymeric surface.

9. The medical device in accordance with claim 8, wherein said polymeric surface is a polyurethane surface.

10. The medical device in accordance with claim 8, wherein said polymeric surface is a polyurethane, a polyurethane copolymer or a silicone rubber polymer.

11. The medical device in accordance with claim 8, wherein the medical device is a component of a catheter, cannula, medical device balloon, or guidewire.

12. The medical device in accordance with claim 8, wherein said covalent linkages between the modified polymeric surface and the spacer component are between carboxyl or hydroxyl groups formed by the radiofrequency discharge treatment on the polymeric surface and primary or secondary amine groups of the spacer component.

13. The medical device in accordance with claim 12, wherein a covalent linkage is present between one or more of said primary or secondary amine groups of spacer component molecules and the acid functionality groups of the anti-thrombogenic, fibrinolytic or thrombolytic agent.

14. A medical device having a biocompatible polymeric surface, wherein said biocompatible polymeric surface comprises a surface which has been modified by subjecting the polymeric surface to radiofrequency discharge treatment within a plasma medium having at least about 40 volume percent water vapor, based upon the total volume of plasma medium, followed by treatment with a coupling agent and a spacer component having amine groups forming covalent linkages with the polymeric surface which had been subjected to radiofrequency discharge treatment with said plasma medium, and then by treatment with an anti-thrombogenic, fibrinolytic or thrombolytic agent having acid functionality contacting and covalently bonding with the spacer component-treated polymeric surface to provide the biocompatible polymeric surface, and said polymeric surface is a silicone rubber surface that had been pretreated with an inert gas plasma.

* * * * *

UNITED STATES PATENT AND TRADEMARK OFFICE
CERTIFICATE OF CORRECTION

PATENT NO.   :   5,132,108
DATED        :   July 21, 1992
INVENTOR(S)  :   Pallassana V. Narayanan and Kimberly D. Stanley It is certified that error appears in the above-indentified patent and that said Letters Patent is hereby corrected as shown below:

Col. 7, line 17-18, "The he sample" should read --The heparinized sample--; line 27, "from 5% water" should read --from 75% water--.

Signed and Sealed this

Tenth Day of January, 1995

Attest:

BRUCE LEHMAN

Attesting Officer    Commissioner of Patents and Trademarks